United States Patent [19]

Telang

[11] 4,388,922
[45] Jun. 21, 1983

[54] SUCTION CANISTER SYSTEM FOR SERIAL COLLECTION OF FLUIDS

[75] Inventor: Anil Telang, Elizabeth, N.J.
[73] Assignee: Becton, Dickinson and Company, Paramus, N.J.
[21] Appl. No.: 287,840
[22] Filed: Jul. 29, 1981
[51] Int. Cl.³ .............................................. A61M 1/00
[52] U.S. Cl. .................................... 604/319; 128/760; 141/35; 604/326
[58] Field of Search ................ 128/276, 760; 137/205; 141/35, 36, 202, 286, 59, 95; 119/14.06, 14.46; 604/326, 319

[56] References Cited

U.S. PATENT DOCUMENTS

| | | | |
|---|---|---|---|
| 1,962,192 | 6/1934 | Hapgood | 119/14.06 |
| 2,006,393 | 7/1935 | Hapgood | 119/14.46 |
| 3,738,381 | 6/1973 | Holbrook | 137/205 |
| 3,863,664 | 2/1975 | Holbrook et al. | 141/35 |
| 4,111,204 | 9/1978 | Hessel | 128/276 |

FOREIGN PATENT DOCUMENTS

WO80/02706 11/1980 PCT Int'l Appl. ................. 128/276

OTHER PUBLICATIONS

Catalog cut, Medi-Vac Corp. Abilene, Texas 79604 1980.

*Primary Examiner*—Richard J. Apley
*Assistant Examiner*—J. L. Kruter
*Attorney, Agent, or Firm*—Richard J. Rodrick

[57] ABSTRACT

A suction canister system for serial collection of fluids comprises a plurality of canisters for collecting fluids. The canisters are in fluid communication with each other so that a vacuum may be applied to the interior of the canisters simultaneously in a parallel-path connection. The fluid connection of the canisters allows fluid to be introduced into the canisters serially.

13 Claims, 7 Drawing Figures

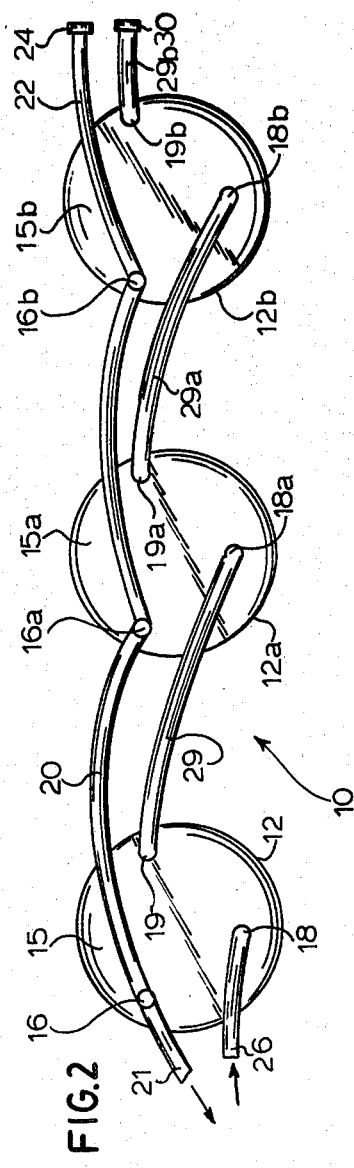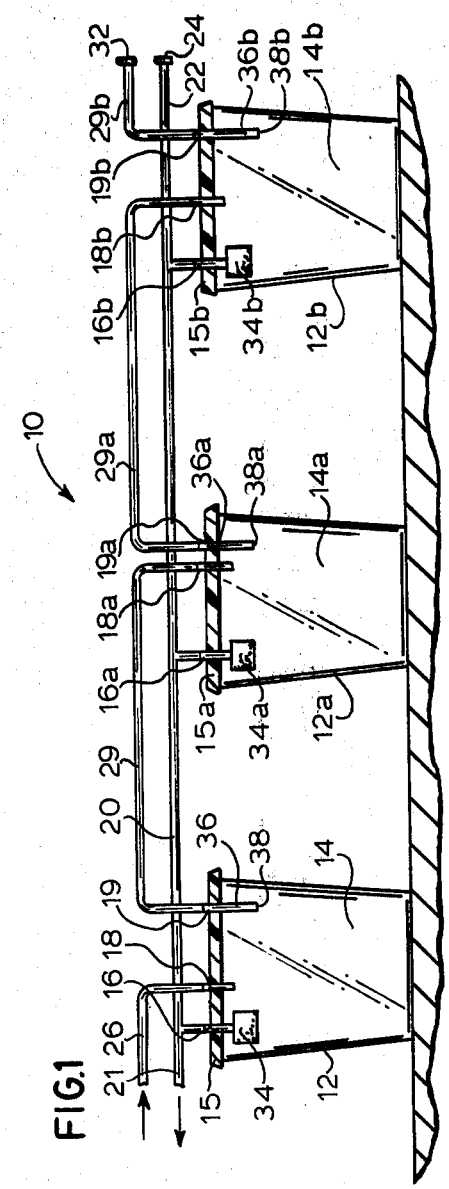

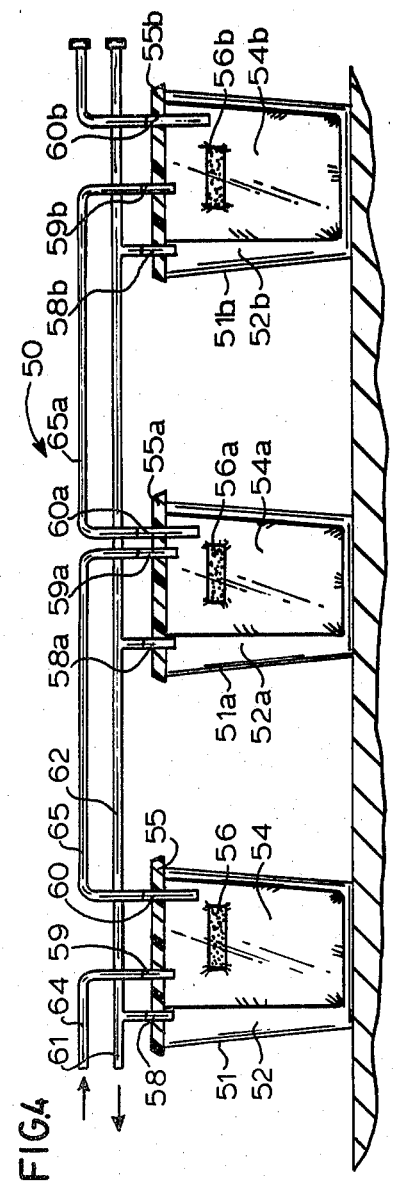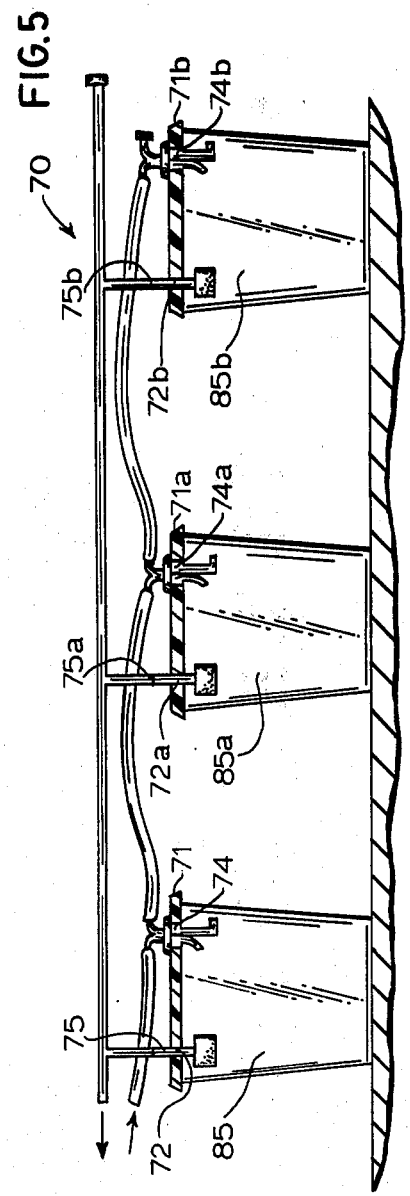

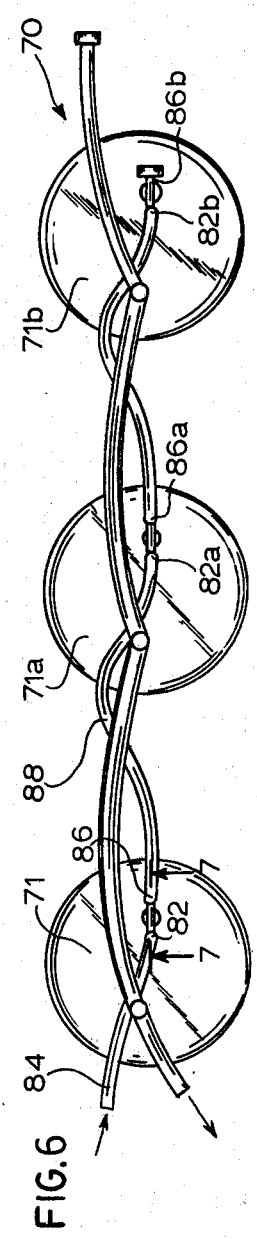
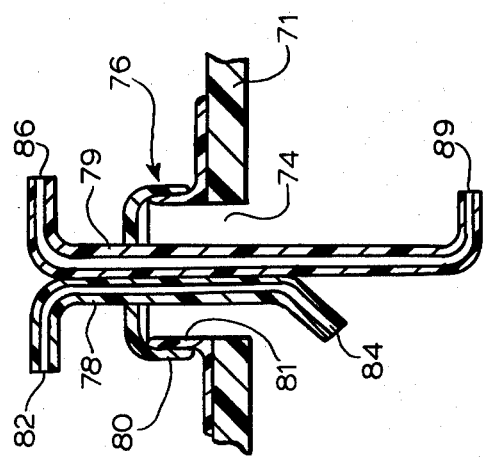
FIG.6
FIG.7

4,388,922

SUCTION CANISTER SYSTEM FOR SERIAL COLLECTION OF FLUIDS

BACKGROUND OF THE INVENTION

1. Field of the Invention

The present invention relates to a suction canister useful in the collection of fluids such as from a patient during a surgical procedure, and more particularly, concerns a suction canister system for the collection of fluids through the system in a serial arrangement.

2. Description of the Prior Art

Suction canisters are employed in the hospital environment, and particularly during surgical procedures, to drain body fluids from a patient. In general, suction canisters employ a collection system and a vacuum source, such as a pump, to facilitate this drainage procedure. Each canister generally includes a flexible line or hose connected to the vacuum source so that vacuum can be applied to the interior of the canister. Another flexible line or hose extends from the canister to the source of body fluids in the patient. Once the vacuum is applied, a negative pressure gradient is communicated through the interior of the suction canister so that body fluids are drawn into the canister.

In many procedures the volume of fluid to be collected exceeds the capacity of a single suction canister used for these purposes. It is, therefore, desirable to be able to collect fluids continuously from the patient without the need to terminate the suction operation. To this end, a serial collection arrangement has been sought whereby a number of suction canisters are connected in fluid communication with each other and when the first suction canister has been filled the fluid travels through appropriate tubing and starts filling the second canister, and so forth. This serial collection arrangement provides an additional benefit in that the single filling procedure might leave some of the canisters unused whereby they can be preserved for further use. One such serial flow suction canister system is described in U.S. Pat. No. 3,863,664.

While the serial flow system of the aforementioned patent is workable and practicable, the advent of improved suction canisters has caused some problems to arise when connecting suction canisters in a serial flow arrangement. In particular, many suction canisters now employ a valve inside the canister, associated with the vacuum port, and typically responsive to the height of fluid in the canister to terminate suction coming in. In order to provide a serial flow connection to a plurality of canisters, the clinicians oftentimes have been instructed to remove the valve in all of the canisters except the last one in the serial flow arrangement. Not only are special instructions involved with this type of manipulation, but the unused valves are normally discarded representing an expenditure for product not being utilized. To further complicate the situation, many suction canisters are now provided with a flexible collection bag inside the canister. When valves are used in suction canisters also employing a flexible collection bag, it is awkward and cumbersome for the clinician to try to remove the valve from the vacuum port. This is due to the fact that the flexible bag is typically sealed to the canister cover completely surrounding the valve. Thus, the clinician has to feel for the valve through the flexible bag and, when removed, the valve would drop into the bag itself to thereby free the vacuum port for fluid flow therethrough in the serial flow arrangement. Such a suction canister with flexible bag and valve is described in U.S. Pat. No. 4,111,204.

Inasmuch as the more recent suction canisters with valves or flexible bags are more difficult to arrange in a serial flow collection combination, improvements are still being sought to facilitate such an arrangement for use in the serial collection of fluids, particularly from patients in the hospital environment. It is to such an improvement that the present invention is directed.

SUMMARY OF THE INVENTION

A suction canister system for serial collection of fluids comprises a plurality of canisters for collecting fluids. Means is included for providing vacuum to the interior of the canisters simultaneously, while fluid is introduced into the canisters serially.

In a preferred embodiment of this aspect of the invention, each canister includes a receptacle and a cover therefor, preferably removable. The cover has a vacuum port therethrough communicating with the interior of the receptacle, a fluid inlet port adapted to permit the flow of fluid therethrough into the receptacle and a fluid outlet port adapted to permit the flow of fluid therethrough out of the receptacle. There is no need for a fluid outlet port in the cover of the last of the plurality of canisters to be filled in the serial collection arrangement, or else such an outlet port is plugged. The vacuum ports of the canisters are connected in parallel fluid communication with each other and are adapted to be connected to a source of vacuum. The inlet port on the canister first in the serial line for collection of fluids is adapted to be connected to a source of fluid outside of the canister system. A serial fluid flow arrangement is established by a connection between the outlet port of a canister to the inlet port on a successive canister in running succession whereby fluid is adapted to be collected in the canisters successively.

Another aspect of the present invention is a suction canister for the collection of fluids therein. The suction canister of the present invention comprises a receptacle for the collection of fluids. A cover for the receptacle includes a vacuum port, a fluid inlet port and a fluid outlet port adapted to permit the flow of fluid therethrough out of the receptacle when connected to a source of vacuum.

While the suction canister system of the present invention provides a serial fluid flow arrangement in canisters without valve controls, it is particularly adapted to be employed in suction canisters normally including a valve associated with the vacuum port. Furthermore, the present suction canister system is adapted to provide a serial fluid flow arrangement for canisters which include a flexible bag therein for the collection of fluids. In the flexible bag suction canisters, there is normally a separation of vacuum applied to the interior of the canister so that vacuum is applied to the interior of the bag as well as to the space inside of the canister but exterior to the bag. The present invention provides a readily assembled system for the serial fluid flow arrangement without disturbing the separation of vacuum feature which flexible bag suction canisters utilize.

In accordance with the principles of the present invention, a suction canister system allows the serial collection of fluids into the individual canisters. The independency of fluid collection contemplated by the present invention allows convenient canister connection in the fluid collection arrangement for as many canisters as might be required for the operation at hand. In the same fashion, removal of an unused canister is simplified. A further advantage is that gradual drainage of fluid lines occurs upon the completion of suctioning through the system. This prevents splashing or spillage of the collected fluid, which may be contaminated, during dismantling of the canister system.

BRIEF DESCRIPTION OF THE DRAWINGS

FIG. 1 is a side elevational view of one embodiment of the present invention illustrating a suction canister system including canisters with valves for vacuum control;

FIG. 2 is a top plan view of the suction canister system of FIG. 1;

FIG. 4 is a side elevational view of another embodiment of the suction canister system of the present invention with each canister including a flexible fluid collection bag and a valve for fluid control;

FIG. 5 is a side elevational view of the suction canister system of the present invention utilizing an alternate fluid line connection arrangement with canister covers having only two holes therethrough;

FIG. 6 is a top plan view of the suction canister system of FIG. 5; and

FIG. 7 is an enlarged cross-sectional view of the fluid line connection arrangement taken along line 7—7 of FIG. 6.

DETAILED DESCRIPTION

Figure 3:
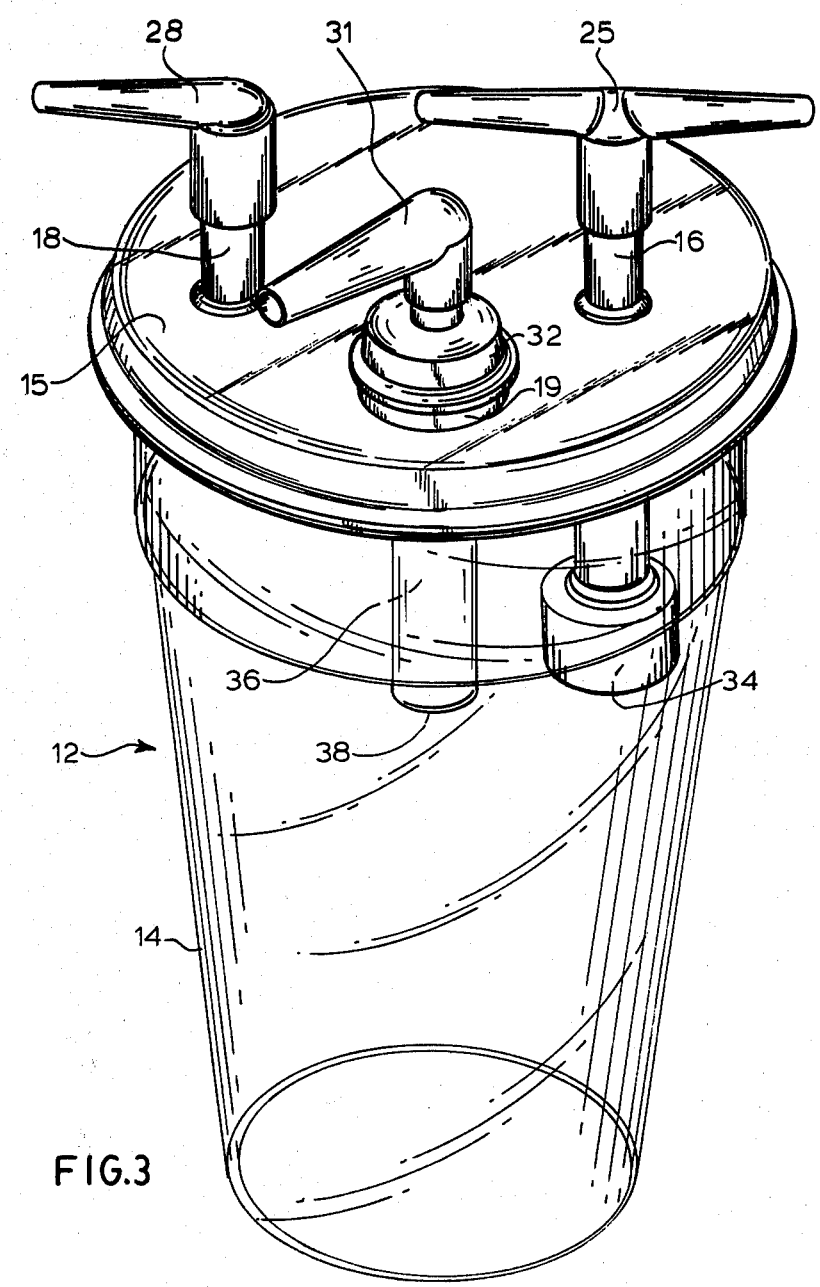
FIG. 3 is an enlarged perspective view illustrating one suction canister of the suction canister system of FIG. 1.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Referring now to the drawings and FIGS. 1-3 in particular, there is illustrated a suction canister system 10 as it may appear utilizing the principles of the present invention and including three canisters 12, 12a and 12b, respectively. (The suffixes "a" and "b" will be used hereinafter to designate similar elements on successively arranged canisters in suction canister system 10.) While the drawings herein illustrate three such suction canisters for purposes of describing exemplary embodiments of the present invention, it is understood that for serial collection of fluids at least two such canisters are needed with there being no limit on the maximum number, except for practical reasons. Also, while it is typical that a suction canister system for serial collection of fluids would employ similar canisters throughout the system, such as illustrated in FIGS. 1 and 2, it is understood that there may be a mix of different canisters in any particular system. For example, some canisters may include flexible bags or valves for vacuum control, whereas other canisters may not include these elements. It is important with respect to the present invention that each suction canister system provide the means for applying vacuum to the interior of the canisters simultaneously while being able to introduce fluid into each canister serially. In the embodiment of FIGS. 1-3, each canister includes a receptacle 14 for collection of fluids therein. Typically, the receptacles are clear, rigid plastic holding anywhere from about 1,000-3,000 cubic centimeters of fluid. Each receptacle 14 is normally cupshaped with an open top; the top is sealed preferably with a removable cover 15. Plastic is usually employed in the fabrication of cover 15. In the embodiment of FIGS. 1-3, cover 15 includes three separate fluid ports therethrough: a vacuum port 16, a fluid inlet port 18 and a fluid outlet port 19. All of the aforementioned ports communicate with the interior of receptacle 14. All of the vacuum ports 16, 16a and 16b are connected in parallel by a length of preferably flexible tubing 20 through which each of these vacuum ports are in fluid communication. Vacuum tubing 20 has an end 21 adapted to be connected to a source of vacuum so that suction can be delivered simultaneously to all the individual canisters in suction canister system 10. It is noted in the embodiment being described, that vacuum tubing 20 has a second end 22 which is capped by a removable plug 24. This, of course, allows the present suction canister system to be modified to include additional canisters, if necessary. The plug contributes to the preservation of vacuum in the system. It can be seen by referring particularly to FIG. 3 that an appropriate T connector 25 may be provided with respect to vacuum port 16 so that suction can flow into each receptacle through vacuum port 16 while being simultaneously fed to the remaining canisters in the suction system. It is understood that T connector 25 is merely a preferable element since other parallel fluid connection schemes may be devised which fall within the purview of the present invention.

In the embodiment of FIGS. 1-3, tubing 26, preferably flexible in nature, is connected to fluid inlet port 18. Tubing 26 is adapted to be connected to a source of fluid outside of the canister system, such as in a patient's body during a surgical procedure. As seen by referring briefly to FIG. 3, an appropriate connector 28 on cover 15 permits the ready connection to tubing 26. In order to provide fluid transfer from one canister to the next, tubing 29 interconnects fluid outlet port 19 on canister 12 with fluid inlet port 18a on canister 12a; similarly, tubing 29a interconnects outlet port 19a on canister 12a with fluid inlet port 18b on canister 12b. Tubing 29b extends from fluid outlet port 19b on canister 12b but is capped by removable plug 30. This not only seals the fluid in the last suction canister, but also prevents loss of vacuum therethrough. It is appreciated that for convenience of operational procedure, the individual suction canisters are normally similar in structure, thereby having the three individual ports as described above. In such case, it becomes necessary to seal or plug the fluid outlet opening on the last canister in the serial line arrangement. On the other hand, the last of the canisters in the serial line arrangement may be fabricated with no fluid outlet port thereby eliminating this capping requirement. Each canister includes an appropriate connector 31 on its cover to permit the connection of tubing 29 to the aforementioned ports.

It should be pointed out that in many instances fluid outlet port 19 is designed to serve a dual purpose: permit fluid to flow out of the receptacle when the receptacle has been filled, and also serve as a pour spout if any of the fluid in the receptacle should be decanted. To this end, connector 31 may be attached to pour spout 19 by means of a snap-on lid 32 which can be readily attached to or removed from port 19 depending upon which mode the port is being utilized.

To exemplify the advantageous features of the present invention, each canister 12, 12a and 12b of the embodiment of FIGS. 1-3 is illustrated including a valve 34 on the interior side of the vacuum port. The purpose of valve 34 is to terminate suction through port 16 when the level of fluid in canister 14 rises to a predetermined level. There are a variety of such valves utilized on suction canisters which are well known in the art. One such valve is a float valve which seals off port 16 by floating against a valve seat associated therewith (not shown) in response to the rising level of fluid in the canister. It is this valve which the operator would have to remove, but for the features of the present invention, in order to provide a serial flow arrangement such as described in U.S. Pat. No. 3,863,664. With the features of the present invention, this valve on the vacuum port can be effectively by-passed. It has been found, however, that should fluid in the canister rise to a level over the valve, some fluids may leak into the vacuum line. This, of course, is most undesirable. Therefore, rather than allow the fluid in receptacle 14 to rise all the way to cover 15, thereby submerging valve 34, an extension tube 36 may be attached to the interior side of each outlet port 19. Tube 36 extends downwardly from outlet port 19 into the receptacle and includes an open distal end 38 positioned at a level inside the receptacle lower than float valve 34. Thus, fluid rising inside the receptacle is drawn first into extension tube 36 before the rising fluid engages the valve. Operation of the embodiment of FIGS. 1-3 will now be described.

Tubing end 21 is connected to a source of vacuum, such as a pump, so that suction is applied in a parallel path to all three canisters simultaneously, the suction being applied to the respective receptacles through vacuum ports 16, 16a and 16b. During a surgical procedure, for example, tubing 26 is inserted into the portion of the patient's body from which fluid is to be drained. The negative pressure in the canisters also provides a negative pressure in tubing 26 so that fluid from the patient is drawn into tubing 26. Fluid travels through tubing 26, fluid inlet port 18 and is collected in receptacle 14. When the level of fluid rises to contact extension tube 36, fluid is then drawn into the extension tube through open distal end 38. The force for drawing fluid into extension tube 36 is the negative pressure in canister 12a which travels through tubing 29 interconnecting fluid outlet port 19 on canister 12 with fluid inlet port 18a on canister 12a. It should be noted that when fluid rises inside receptacle 14, it may continue to rise past opening 38 in extension tube 36. In that case, the rising fluid will contact valve 34 and when the level is high enough, valve 34 will terminate suction through vacuum port 16. Suction is still applied to the interior of the canister through fluid outlet port 19 due to the parallel-path vacuum connection to adjacent canister 12a. Therefore, when canister 12 is essentially filled, fluid then serially travels through tubing 29 and enters canister 12a. This filling procedure continues when canister 12a is essentially filled so that fluid will then travel through tubing 29a and start filling canister 12b. When fluid rises in canister 12b to the level of valve 34b, the valve will close to thereby automatically terminate the vacuum for the entire canister system.

Referring now to FIG. 4, suction canister system 50 is illustrated including canisters 51, 51a and 51b. Inside receptacle 52 is a flexible collection bag 54 sealed to cover 55 and depending into the receptacle. In this embodiment, each flexible bag 54 includes a gas-permeable, liquid-impermeable membrane 56 therein. A canister similar to the type being described with respect to FIG. 4 is disclosed in U.S. Pat. No. 4,111,204. Cover 55 in this embodiment is the same as cover 15 in the previously described embodiment, including a vacuum port 58, a fluid inlet port 59 and a fluid outlet port 60. Vacuum port 58 communicates with the interior of receptacle 52 in the space exterior to collection bag 54 for providing vacuum thereto. Vacuum conditions are communicated from the space exterior to bag 54 through membrane 56 to the interior of the bag. Both fluid inlet port 59 and fluid outlet port 60 are in fluid communication with the interior of collection bag 54 so that vacuum can be applied to the interior of the bag through the fluid outlet port, except for canister 51b, which is the last canister in the fluid collection arrangement.

In operation, tubing end 61 is connected to a source of vacuum so that suction can be applied in a parallel-path simultaneously to the three canisters. Tubing 62 provides this parallel-path by being connected to the respective vacuum ports of the canisters, similar to the previously described embodiment. Tubing 64 is placed in a source of fluid, for example, in the body of a patient during a surgical procedure. Negative pressure in tubing 64 caused by the vacuum conditions in the canisters draws fluid through tubing 64, through fluid inlet 59 and into flexible bag 54. The suction applied to the space exterior to the collection bag through vacuum port 58 contributes to keeping flexible bag 54 expanded during the fluid collection procedure. When fluid inside bag 54 rises to the level where it covers membrane 56, the liquid-impermeable nature of the membrane will prevent fluid from passing thereout. However, at the same time, suction from vacuum port 58 will now be terminated. A suction force remains applied to the interior of the flexible bag by virtue of the vacuum conditions in adjacent canister 51a. In this regard, the negative pressure is applied to the interior of bag 54 through tubing 65 which interconnects fluid outlet port 60 on canister 51 with fluid inlet port 59a on canister 51a. Therefore, when flexible bag 54 on the first canister is filled the negative pressure gradient inside tube 65 will draw fluid through fluid outlet port 60 so that fluid will start filling collection bag 54a in the next canister. This procedure continues until the last canister is filled. In the embodiment being described, when fluid inside flexible bag 54b rises to the level of membrane 56b, all suction forces will be terminated automatically due to the valve-like characteristics of membrane 56b.

Turning now to FIGS. 5-7, an alternate embodiment of the canister covers and tubing interconnections is illustrated. Instead of three separate openings through the cover for the three ports as described in the previous embodiments, cover 71 has only two holes 72 and 74 therethrough. Vacuum port 75 is associated with holes 72; a combined fluid flow assembly 76 is associated with hole 74 through cover 71. As seen more clearly in FIG. 7, a fluid inlet tube 78 is positioned back-to-back with a fluid outlet tube 79. Both are mounted in a lid 80 which is adapted to fit over an annular rim 81 surrounding opening 74. This will allow removal of fluid flow assembly 76 so that hole 74 may be used as a pour spout. Fluid inlet tube 78 includes an exterior opening 82 which is connected to tubing 84 for collection of fluid from the source. An interior opening 84 allows fluid collected from the source to be deposited inside canister 85. Fluid outlet tube 79 is similar to fluid inlet tube 78, although separate therefrom. The outlet tube includes an exterior opening 86 which is adapted to be connected with tubing 88 for interconnecting the outlet port of one canister to the inlet port on a successive canister as seen in FIG. 6. Fluid outlet tube 79 also includes an interior opening 89 which is in fluid communication with the interior of canister 85. It is preferable as seen in FIG. 7 that opening 89 on the outlet tube depend lower into the receptacle than opening 84 on the fluid inlet tube. Thus, fluid rising inside the receptacle can be readily drawn into opening 89 so that when one canister is essentially filled fluid can then be transported in a serial arrangement to the next, successive canister.

In the embodiment of FIGS. 5–7, the vacuum connection to the three canisters is similar to the vacuum connections of the previously described embodiments.

Thus, the present invention provides a suction canister system for serial collection of fluids particularly useful with suction canisters including fluid control valves or fluid collection bags therein. In addition to providing for the serial collection of fluids, the tubing interconnections between canisters are gradually drained of fluid upon completion of suctioning. This advantageously allows the user to dismantle the suction system without splashing or spillage of fluids which may have been in the tubing interconnections. It can also be seen that the present invention also permits the ready addition of canisters to the system if large quantities of fluid are expected, or the removal of canisters which are unused during the fluid collection procedure. Overall, the present invention provides a significant improvement for the users of suction canisters.

What is claimed is:

1. A suction canister system for collection of patient body fluids comprising:
   a plurality of canisters, each canister including a receptacle and a cover having a vacuum port therethrough communicating with the interior of the receptacle, means including a fluid inlet port to permit the flow of fluid therethrough into the receptacle, and means including a fluid outlet port to permit the flow of fluid therethrough out of the receptacle, the last of the plurality of canisters to be filled in the serial collection arrangement including means to prevent fluid from flowing thereout, the vacuum ports of said canisters being connected in parallel fluid communication with each other and having means for connection to a source of vacuum, the inlet port on the canister first in the serial line for collection of fluids having means for connection to a source of fluid outside of the canister system, the outlet port of each canister connected to the inlet port on a successive canister in a serial fluid flow arrangement whereby fluid is collected in said canisters successively.

2. The canister system of claim 1 wherein said means on the last of the plurality of canisters includes the cover of such last canister in the serial line being free of fluid outlet port.

3. The canister system of claim 1 wherein said means on the last of the plurality of canisters includes a cover having a fluid outlet port therethrough and means for sealing this last fluid outlet port.

4. The canister system of claim 3 wherein the means for sealing includes a removable plug on the associated outlet port.

5. The canister system of claim 1 wherein at least one canister further includes a valve connected to the vacuum port on the interior side thereof in the receptacle, said valve terminating suction through the vacuum port when fluid inside the receptacle contacts said valve, with suction being applied to the interior of said canister through the fluid outlet port due to the parallel-path vacuum connection to the remaining canisters in said system whereby when one canister is filled fluid travels through the outlet port and into the next-connected canister through its inlet port for successive collection therein.

6. The canister system of claim 1 wherein at least one canister includes a flexible collection bag positioned in the receptacle and means for providing vacuum to the interior of said collection bag and to the space inside said receptacle and exterior to said collection bag.

7. The canister system of claim 6 wherein the vacuum port communicates with said space exterior to said collection bag for providing vacuum thereto.

8. The canister system of claim 6 wherein both the fluid inlet and fluid outlet ports of said canister with said bag are in fluid communication with the interior of said collection bag with vacuum being applied to the interior of said bag through the fluid outlet port except for said last canister in the fluid collection arrangement.

9. The canister system of claim 7 wherein the collection bag of said canister includes a gas-permeable, liquid-impermeable member therein serving as a valve to terminate suction therethrough from said vacuum port.

10. The canister system of claim 1 wherein each of said ports in said cover is associated with a separate hole through said cover.

11. The canister system of claim 1 wherein at least one canister has a cover including only two holes therethrough, the vacuum port associated with one of said holes and the fluid inlet and fluid outlet ports associated with the other of said holes.

12. The canister system of claim 11 wherein said fluid inlet port includes a first tube and said fluid outlet port includes a second tube, each tube extending through the other of said holes and separately communicating with the interior of the receptacle.

13. The canister system of claim 1 wherein all of said canisters have a cover including only two holes therethrough, the vacuum port associated with one of said holes and the fluid inlet and fluid outlet ports associated with the other of said holes.

* * * * *